United States Patent [19]

Hofer et al.

[11] Patent Number: 5,700,825
[45] Date of Patent: Dec. 23, 1997

[54] RADIOSENSITIZING DIAMINES AND THEIR PHARMACEUTICAL PREPARATIONS

[75] Inventors: Kurt G. Hofer; Li-xi Yang, both of Tallahassee, Fla.

[73] Assignee: Florida State University, Tallahassee, Fla.

[21] Appl. No.: 414,272

[22] Filed: Mar. 31, 1995

[51] Int. Cl.$^6$ .................... A61K 31/415; C07D 233/95; C07D 233/91
[52] U.S. Cl. ........................... 514/397; 548/313.7
[58] Field of Search ................ 548/313.7; 514/397

[56] References Cited

U.S. PATENT DOCUMENTS

| | | | |
|---|---|---|---|
| 4,282,232 | 8/1981 | Agrawal | 424/267 |
| 4,323,689 | 4/1982 | Vogel et al. | 548/336 |
| 4,371,540 | 2/1983 | Lee et al. | 424/273 R |
| 4,456,610 | 6/1984 | Hofheinz et al. | 424/273 R |
| 4,462,992 | 7/1984 | Agrawal et al. | 424/180 |
| 4,665,191 | 5/1987 | Waddill et al. | 548/336 |
| 4,995,898 | 2/1991 | Nasu et al. | 71/90 |
| 5,073,566 | 12/1991 | Lifer et al. | 514/381 |
| 5,073,639 | 12/1991 | Suto | 548/339 |
| 5,215,738 | 6/1993 | Lee et al. | 424/10 |
| 5,236,944 | 8/1993 | Distelmans et al. | 514/397 |
| 5,270,330 | 12/1993 | Suzuki et al. | 514/398 |
| 5,371,101 | 12/1994 | Itoh et al. | 514/383 |
| 5,389,661 | 2/1995 | Sircar et al. | 514/381 |

FOREIGN PATENT DOCUMENTS

| | | | |
|---|---|---|---|
| 519633 | 12/1955 | Canada. | |
| 784711 | 5/1968 | Canada. | |
| 0 544 412 A2 | 6/1993 | European Pat. Off. | A61K 49/02 |
| 2-193979 | 7/1990 | Japan | C07D 233/91 |
| 6-345728 | 12/1994 | Japan | 207/30 |
| 2076402 | 12/1981 | United Kingdom. | |
| WO 93/13075 | 7/1993 | WIPO | C07D 233/61 |

OTHER PUBLICATIONS

Hay et al., Hypoxia–selective antitumor agents. 10. Bis (nitroimidazoles) and related Bis(nitroheterocycles): Development of derivatives with higher rates of metabolic activation under hypoxia and improved aqueous solubility. J. Med. Chem., vol. 38, No. 11, pp. 1928–1941; May 26, 1995.

Gatenby et al., "Oxygen Distribution in Squamous Cell Carcinoma Metastases And Its Relationship to Outcome of Radiation Therapy", Int. J. Radiat. Oncol. Biol. Phys.14; 831–822(1988).

Berg and Sharp, "Derivatives of 4– and 5–nitro–2–methylimidazol–1–yl–acetaldehyde", European Journal of Med. Chemistry 10:171–177 (1975).

Huang and Swern, "Oxidation of Long–Chain and Related Alcohols to Carbonyls by Dimethyl Sulfoxide Activated by Oxalyl Chloride[1]", J. Organic Chemistry 43:2480–2482 (1978).

Holley et al., Biochem. Pharmacology, 43(4) 763–769 (1992).

Carminati et al., Biochem. Pharmacology, 38(14) 2253–2258 (1989).

*Primary Examiner*—Jose G. Dees
*Assistant Examiner*—Laura R. Cross
*Attorney, Agent, or Firm*—Senniger, Powers, Leavitt & Roedel

[57] ABSTRACT

A compound comprising a diamine containing from 2–4 electron-affinic radiosensitizing functional groups or a salt thereof is provided. In a preferred embodiment the compound has the formula

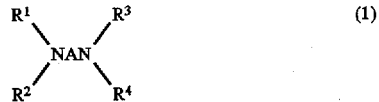

(1)

wherein A comprises a carbon chain having from about 2–10 carbons in the chain, $R^1$, $R^2$, $R^3$, and $R^4$ are H, or T, T is

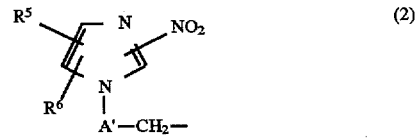

(2)

wherein A' comprises a carbon chain having from about 1–8 carbons in the chain, $R^5$ is H, lower alkyl, or halo, and $R^6$ is H, lower alkyl, halo or nitro, provided that at least one of $R^1$ and $R^2$, and at least one of $R^3$ and $R^4$ is T. Intermediates for, pharmaceutical compositions containing, methods for making and methods for using such compounds to radiosensitize and kill hypoxic tumor cells are also provided.

33 Claims, No Drawings

RADIOSENSITIZING DIAMINES AND THEIR PHARMACEUTICAL PREPARATIONS

BACKGROUND OF THE INVENTION

This invention relates to novel radiosensitizing compounds, and in particular to substituted diamines containing 2–4 electron-affinic radiosensitizing functional groups, their pharmaceutical preparations, and methods of making and using this new class of highly potent radiosensitizers of hypoxic tumor cells.

In the United States, alone, over a half million patients undergo radiation therapy each year as a part of their battle against cancer. To date, however, radiation therapy has produced only limited success as a cancer treatment. Understandably, therefore, a major effort has been underway for a number of years to develop means to improve the efficacy of such radiotherapy techniques.

It is widely believed that the presence of radioresistant, hypoxic (poorly oxygenated) cells in tumors constitutes a significant factor in causing local failure in conventional cancer radiotherapy. For example, it was reported by Gatenby et al., Int. J. Radiat. Oncol. Biol. Phys. 14: 831–833 (1988), that for head and neck tumors, the hypoxic cell volume is inversely correlated with tumor radiosensitivity. Other reports confirm this conclusion for a variety of types of tumors and suggest that the presence of a concentration of as little as 2–3% hypoxic cells in a tumor may double the radiation dose required for tumor control.

Various solutions have been proposed to overcome the problem of hypoxia, including carrying out radiation treatments in high pressure oxygen chambers and the substitution of "fast neutron" or $\pi$ meson radiation in place of x-rays. However, these techniques are not wholly satisfactory for a number of reasons, including the great expense and difficulty frequently associated with such procedures.

One promising field of investigation for dealing with radioresistant hypoxic tumor cells has been the use of "radiosensitizing" compounds which selectively increase the sensitivity of hypoxic cells to radiation. This specificity to hypoxic cells is also valuable because a significant percentage of solid tumors are characterized by such cells while most normal tissue is not. Thus, treatment with such compounds serves to enhance the impact of radiation on tumor cells while having little effect on the impact of radiation on healthy cell tissue. A number of heterocyclic, electron-affinic compounds, and in particular, those with oxidized nitrogen moieties, have been successfully used for the purpose of radiosensitizing hypoxic tumor cells. Specifically, the discovery that the nitroimidazoles metronidazole (metro) and misonidazole (miso) sensitize hypoxic cells to radiation provided initial optimism for a breakthrough solution to the problem of tumor hypoxia. Unfortunately, however, both agents have proven to be highly toxic at therapeutic levels. Thus, it is clear that a need exists for more potent radiosensitizing compounds which can be administered at lower doses to reduce toxic side effects.

SUMMARY OF THE INVENTION

Among the several objects of the invention, therefore, may be noted the provision of a novel class of hypoxic tumor-targeted radiosensitizing agents for cancer radiation therapy. Such compounds, which comprise diamine derivatives containing from 2 to 4 electron-affinic radiosensitizing functional groups, provide greatly enhanced radiosensitization of hypoxic tumors and thus reduced toxic side effects to normal body tissues at a given dosage. Also provided are intermediates and methods for the preparation of such radiosensitizing compounds, and techniques for the use of such compounds and pharmaceutical preparations containing them in the radiosensitization of hypoxic tumor cells and the destruction of such tumor cells in warm-blooded animals.

Briefly, therefore, the present invention is directed to novel compounds comprising diamines which contain from 2–4 electron-affinic radiosensitizing function groups, or salts thereof. The invention is further directed to pharmaceutical compositions for radiosensitizing hypoxic tumor cells which contain a radiosensitizing amount of the above described diamines or a pharmaceutically acceptable salt thereof in admixture with a pharmaceutically acceptable carrier.

The present invention further relates to compositions containing intermediates useful for the preparation of preferred diamines of the invention which compositions comprise nitroimidazole compounds or derivatives thereof wherein at least about 50% by weight of the nitroimidazole compounds or derivatives thereof contained in the composition comprise aldehydes having the formula:

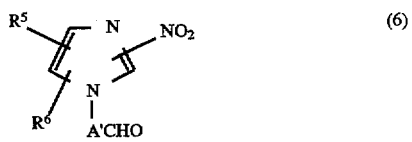

wherein $R^5$ is hydrogen, lower alkyl or halo, $R^6$ is hydrogen, lower alkyl, halo or nitro, and A' comprises a carbon chain having from about 1–8 carbons in the chain.

In another aspect of the invention, a method is provided for making preferred diamines of the invention of the formula

wherein A comprises a carbon chain having from about 2 to 10 carbons in the chain, $R^1$, $R^2$, $R^3$, and $R^4$ are H or T, T is

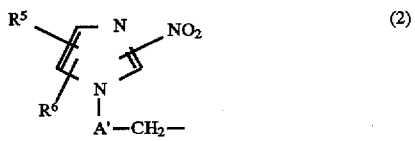

wherein A' comprises a carbon chain having from about 1–8 carbons in the chain, $R^5$ is H, lower alkyl, or halo, and $R^6$ is H, lower alkyl, halo or nitro, provided that at least one of $R^1$ and $R^2$, and at least one of $R^3$ and $R^4$ is T, which method includes the steps of (a) converting a compound of formula

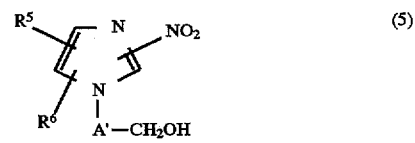

to a compound of formula

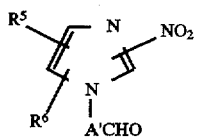 (6)

using dimethyl sulfoxide activated by oxalyl chloride, and (b) treating the compound of formula

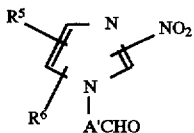 (6)

with a diamine having about 2 to 10 carbons in its main chain in the presence of an organic acid and a reducing agent.

In still another aspect of the invention, a method of radiosensitizing hypoxic tumor cells is provided which comprises administering a radiosensitizing amount of the pharmaceutical composition described above to the hypoxic tumor cells. Related thereto, a method is also provided for killing hypoxic tumor cells in a warm-blooded animal which includes the steps of administering to the warm-blooded animal a pharmaceutical composition as described above in an amount effective to radiosensitize the hypoxic tumor cells, followed by, after a time interval sufficient to enhance radiosensitization of the hypoxic tumor cells, irradiating the hypoxic tumor cells with a dose of radiation effective to kill the hypoxic tumor cells.

Other objects and features will be in part apparent and in part pointed out hereinafter.

DETAILED DESCRIPTION OF THE PREFERRED EMBODIMENTS

In accordance with the present invention, multi-functional diamine derivatives made according to the methods described below have been prepared which exhibit up to 400 times the radiosensitizing potency of mono-functional radiosensitizing compounds such as metro. Moreover, it has been demonstrated, using the in vitro colony forming assay for evaluating cell survival, that treatment with representative substituted diamines of the type described herein under mild hyperthermic conditions is so effective that hypoxic cells actually became more radiosensitive that fully oxic cell populations. As a result, such greatly increased potency permits the administration of much lower dosages of these compounds for the same or even greater radiosenisitization of hypoxic tumor cells, allowing for a concomitant reduction in toxic side effects on healthy tissue for any particular dosage level required to effectively radiosensitize the hypoxic tumor cells.

Without being bound by any particular theory, it is hypothesized that the remarkably higher potency exhibited by this class of compounds is due to the synergistic combination of at least two factors. First, the diamine moiety is mildly basic. This is thought to serve as a mechanism for targeting the attached radiosensitizing moieties toward the predominantly acidic hypoxic tumor cells. Further, the diamine is likely to be attracted within such cells to deoxyribonucleic acid (DNA) which is acidic in character, due to its high phosphate content. Second, their greatly enhanced sensitizing potency may also be related to the mechanism of radiation-induced cell death. It is thought that multiple ionizations may be required at or near the DNA for low levels of radiation to cause cell death. Thus, molecules containing multiple radiosensitizing functional groups may be capable of participating in more than one local ionizing event without requiring the close proximity of additional molecules.

This novel class of potent radiosensitizers comprise substituted diamines containing from 2 to 4 electron-affinic, radiosensitizing functional groups. Preferably, the substituted diamines of the invention comprise those having the general formula:

 (1)

wherein A' comprises a carbon chain having from about 2–10 carbons in the chain, $R^1$, $R^2$, $R^3$, and $R^4$ are H or T, T is

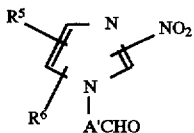 (2)

wherein A' comprises a carbon chain having from about 1–8 carbons in the chain, $R^5$ is H, lower alkyl, or halo, and $R^6$ is H, lower alkyl, halo or nitro. In the preferred embodiment, at least one of $R^1$ and $R^2$, and at least one of $R^3$ and $R^4$ is T.

Most preferably, A is alkylene, T is 2-, 4-, or 5-nitroimidazolyl alkyl, particularly 5-nitroimidazolyl alkyl, $R^5$ is ethyl or methyl, particularly 2-methyl, $R^6$ is H, methyl or nitro, particularly H, and A' is ethylene or methylene, particularly methylene. Such particularly preferred compounds may have either the formula:

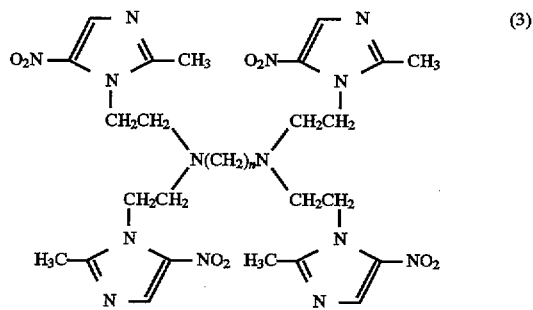 (3)

DATM or

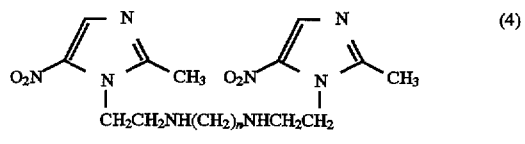 (4)

DADM (n = 2–10)

Specific preferred compounds of the present invention include diaminetetrametronidazoles (DATMs) such as N, N, N', N'-tetra[2'-(2-methyl-5-nitro-1-imidazolyl)ethyl]-1,4-butanediamine; N, N, N', N'-tetra[2'-(2-methyl-5-nitro-1-imidazolyl)ethyl]-1,5-pentanediamine; and N, N, N', N'-tetra[2'-(2-methyl-5-nitro-1-imidazolyl)ethyl]-1,8- octanediamine; and diaminedimetronidazoles (DADMs) such as N, N'-di[2'-(2-methyl-5-nitro-1-imidazolyl)ethyl]-1, 4-butanediamine; N, N'-di[2'-(2-methyl-5-nitro-1-imidazolyl)ethyl]-1,5-pentanediamine; and N, N'-di[2'-(2-methyl-5-nitro-1-imidazolyl)ethyl]-1,8-octanediamine.

The radiosensitizing compounds of the present invention are prepared by linking two or more electron-affinic radiosensitizing functional groups to the terminal nitrogens of a diamine using an appropriate reaction scheme. For example, preferred diamines of the formula:

wherein A comprises a carbon chain having from about 2–10 carbons in the chain, $R^1$, $R^2$, $R^3$, and $R^4$ are H or T, T is

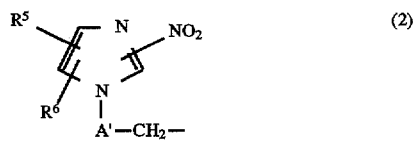

wherein A' comprises a carbon chain having from about 1–8 carbons in the chain, $R^5$ is H, lower alkyl, or halo, $R^6$ is H, lower alkyl, halo or nitro, and in which at least one of $R^1$ and $R^2$, and at least one of $R^3$ and $R^4$ is T, are prepared by a two-step process in which nitroimidazoles of formula

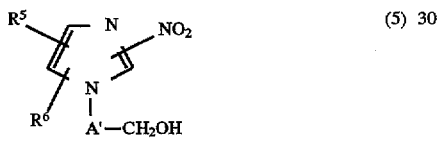

are oxidized using a mild oxidant, dimethyl sulfoxide activated by oxalyl chloride, under conditions favorable to form an aldehyde having the formula

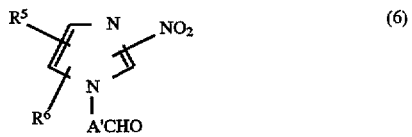

The aldehyde thus prepared is then treated with a diamine having about 2 to 10 carbons in its main chain in the presence of an organic acid and a reducing agent to obtain the substituted diamine.

The formation of the key aldehyde intermediate in the above reaction scheme has been exceedingly difficult to achieve. Berg and Sharp, European Journal of Med. Chemistry 10: 171–177 (1975), reported a method to produce a crude mixture containing approximately 30% of 2-methyl-5-nitroimidazol-1-yl-acetaldehyde in a complex with the unchanged alcohol. However, their attempts to isolate free aldehyde from this mixture resulted in its decomposition. Oxidation of metronidazole using chromic acid, chromic acid-pyridine, tert-butyl chromate, silver carbonate on celite and 1-chlorobenztriazole only produced the corresponding acid. When the oxidation by chromic acid was performed at room temperature, a mixture containing about 7% of 2-methyl-5-nitroimidazol-1-yl-acetaldehyde was obtained. Berg and Sharp used potassium dichromate-acetic acid to oxidize metronidazole, but were only able to obtain a mixture containing up to 30% aldehyde which, as mentioned, could not be isolated without decomposing.

Conversion to the aldehyde was also difficult to achieve because nitroimidazoles do not readily dissolve in solvent solutions in which the oxidation may be carried out. However, applicants have discovered that nitroimidazoles can be dissolved for such oxidation reactions using dimethyl sulfoxide.

Accordingly, applicants have developed a process in which a composition is produced containing greater than 50% by weight (of the total concentration of nitroimidazoles and their derivatives in the composition) of the described nitroimidazolylalkyl aldehydes in a mixture of nitroimidazoles and nitroimidazole derivatives and from which the isolated and purified aldehydes may be obtained. The process is carried out using a modified Swern oxidation reaction (see Huang and Swern, J. Organic Chemistry 43: 2480–2482, 1978), at a reaction mixture temperature of between about –45° C. and about –65° C., preferably at about –50° C. The dimethyl sulfoxide activated using oxalyl chloride reacts with alcohols to form alkoxysulfonium salts. The alkoxysulfonium salts are readily converted to carbonyl compounds upon addition of triethylamine or the like to form the corresponding aldehyde. Applicants have further discovered that the results are enhanced substantially if the reaction mixture is heated (e.g., by removing dry ice and acetone used as a cold source) for no more than about 10 minutes at the conclusion of the oxidation step, prior to commencing the reductive amination of the aldehyde described below.

The disclosed oxidation process step used, e.g., to form 2-methyl-5-nitroimidazol-1-yl-acetaldehyde, which has the following structural formula:

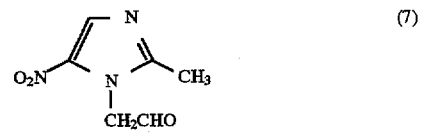

is illustrated by the following reaction scheme:

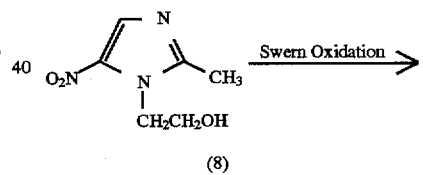

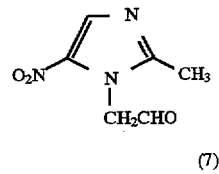

CH$_2$Cl$_2$ is added to oxalyl chloride under nitrogen gas. The solution is cooled to –50° C. and Me$_2$SO is then added dropwise to the stirred solution. Metronidazole [1-(2-hydroxyethyl)-2-methyl-5-nitroimidazole] dissolved in Me$_2$SO is added. After additional stirring, triethylamine is added, and the reaction mixture is stirred again and allowed to warm to room temperature. The resultant mixture is diluted, washed, extracted, filtered and dried to obtain the isolated and substantially purified aldehyde.

The preferred di- and tetra-nitroimidazolylalkyl diamines are synthesized by the reaction of the aldehyde intermediates described above with diamines having about 2 to 10 carbons in their main chain in the presence of an organic acid and a mild reducing agent, via reductive amination as shown in the following reaction scheme.

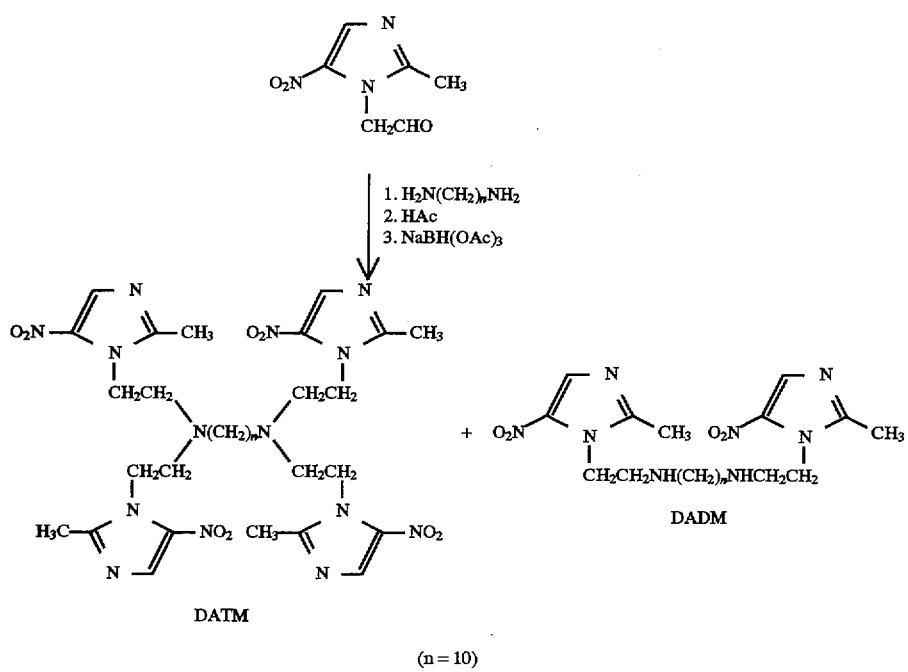

(n = 10)

Sodium triacetoxyborohydride [NaBH(OAc)₃] is advantageously used as a mild and selective reducing agent in the reduction step. The reaction mixture in the reduction step is acidified using an organic acid, preferably acetic acid. The reaction proceeds most favorably when the relative amounts of reactants is controlled to produce a molar ratio of aldehyde to diamine of about 4.1 to 1.

The reaction described above has the advantage of being an efficient and convenient "one vessel" reaction that permits simultaneous preparation of both di- and tetranitroimidazolylalkyl diamines.

Because reaction symmetry favors the addition of either two or four functional groups during reductive amination, the attachment of an appropriate blocking group to one of the terminal amines is required in order to form a substituted diamine containing three radiosensitizing functional groups.

The compounds of the present invention are advantageously converted to their corresponding salts to assist in their formulation into water soluble pharmaceutical compositions. Examples of pharmaceutically acceptable salts include the salts formed by reaction of the substituted diamines of the invention with gluconic acid, HCl, H₃PO₄, maleic acid, oxalic acid, acetic acid, sulfonic acid, sulfuric acid nicotinic acid, glucuronic acid and lactobionic acid. Methods for obtaining such salts are illustrated in Example 5 below.

The diamine derivatives of the present invention, particularly in the form of the salts just described, can be combined with various excipient vehicles and/or adjuvants well known in this art which serve as pharmaceutically acceptable carriers to permit drug administration in the form of, e.g., injections, suspensions, emulsions, tablets, capsules, and ointments. These pharmaceutical compositions, containing a radiosensitizing amount of the described substituted diamine compounds, may be administered by any acceptable means which results in the radiosensitization of hypoxic tumor cells. For warm-blooded animals, and in particular, for humans undergoing radiotherapy treatment, administration can be oral, parenteral, subcutaneous, intravenous, intramuscular and/or intraperitoneal. To destroy hypoxic tumor cells, the pharmaceutical composition containing the radiosensitizing diamines are administered in an amount effective to radiosensitize the hypoxic tumor cells (in the range of 1 to 100 mg/kg for humans). The specific dosage administered will be dependent upon such factors as the general health and physical condition of the patient as well as his age and weight, the stage of the patient's disease condition, and the existence of any concurrent treatments.

After administration of the radiosensitizing composition to the hypoxic tumor cells and the passage of a time interval sufficient to enhance radiosensitization of the hypoxic tumor cells, the hypoxic tumor cells are irradiated with a dose of radiation effective to destroy the hypoxic tumor cells. Generally, the patient will receive a total radiation dosage of about 60 to 76 Gy over seven to eight weeks, each individual radiation dose to be given within approximately 1 to 4 hrs after administration of the radiosensitizer. Such sequences of radiosensitization treatments and irradiation are repeated as needed to abate and, optimally, reduce or eliminate, the spread of the malignancy.

The radiosensitization provided by the radiosensitizing diamines of the present invention is significantly enhanced when combined with concurrent heat treatment of the hypoxic tumor cells. Such heat treatment may be carried out, e.g., by immersion in a warm water bath preheated to a temperature of from about 37° C. to about 41° C., or by local heating of tumors with microwave applicators.

To further illustrate and explain the invention, several examples are presented below.

EXAMPLE 1

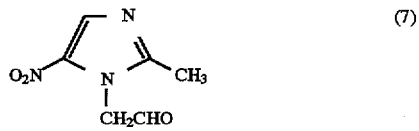

(7)

Preparation of 2-methyl-5-nitroimidazol-1-yl-acetaldehyde

To 160 ml of $CH_2Cl_2$ was added dropwise 2 ml (22 mmol) of oxalyl chloride under nitrogen gas. The solution was cooled to −50° C. and 17 ml (240 mmol) of $Me_2SO$ was added dropwise to the stirred solution. About 20 min later, 3.42 g (20 mmol) of metronidazole [1-(2-hydroxyethyl)-2-methyl-5-nitroimidazole] dissolved in 15 ml of $Me_2SO$ was added. After 20 min of additional stirring, 33 ml (240 mmol) of triethylamine was added. The reaction mixture was stirred for another 10 min and then allowed to warm to room temperature. The mixture was diluted with 400 ml of ethyl acetate and washed 4 times with water, first with 100 ml and then 3 times with 50 ml. The 250 ml water volume was extracted 3 times with 250 ml of ethyl acetate and the ethyl acetate was added to the $CH_2Cl_2$. The mixture was washed with 100 ml of saturated NaCL solution, dried over anhydrous $MgSO_4$, filtered, and concentrated to dryness in a rotary evaporator. The resulting crude residue was purified by flash silica gel chromatography to give the pure desired aldehyde (2-methyl-5-nitroimidazol-1-yl-acetaldehyde).

The chemical structure of the resulting pure aldehyde was evaluated by $^1H$ NMR ($CDCl_3$, 300 MHz) δ 9.76 (s, 1H, CHO), 7.99 (s, 1H, imidazole H), 5.21 (s, 2H, $CH_2CHO$), 2.41 (s, 3H, $CH_3$).

EXAMPLE 2

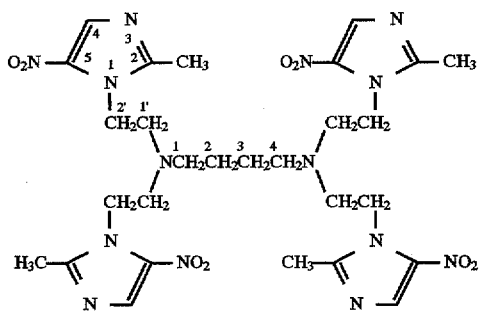

Preparation of N, N, N', N'-tetra [2'-(2-methyl-5-nitro-1'-imidazolyl)ethyl]-1,4-butanediamine The 2-methyl-5-nitroimidazol-1-yl-acetaldehyde (3.0 g, 17.6mmol) synthesized by the procedure described in Example 1 was dissolved in 80 ml of 1, 2-dichloroethane, 0.44 ml of butanediamine (4.4 mmol) was added, the reaction mixture was stirred for 30 min and then acidified with 1 ml of acetic acid (17.6 mmol). Then 4.48 g of sodium triacetoborohydride (21.12 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous $NaHCO_3$ and 30 ml of water. The aqueous solution was combined for further extraction of compound (5). The organic layer was dried over anhydrous $MgSO_4$, and the solvent was evaporated to leave residual oil which solidified at 4° C. for 2 days. The obtained solid was recrystallized from ethyl acetate/hexane to give N, N, N', N'-tetra[2'-(2-methyl-5-nitro-1-imidazolyl)ethyl]-1,4-butanediamine (m.p. 194°–196° C.).

The chemical structure of the target compound was evaluated by $^1H$ NMR ($CDCl_3$, 300 MHz) δ 7.93 (s, 4H, imidazole H4); 4.28 (t, J=6.6 Hz, 8H, H2'); 2.81 (t, J=6.6 Hz, 8H, H1'); 2.55–2.52 (m, 4H, H1, H4); 2.52 (s, 12H, imidazole Me2); 1.25–1.23 (m, 4H, H2, H3).

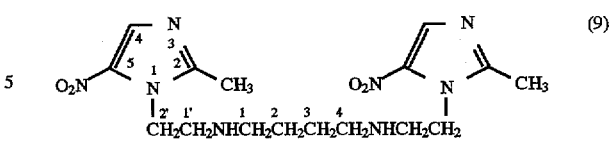

Preparation of N, N'-di[2-(2-methyl-5-nitro-1-imidazolyl)-1,4-butanediamine

The above combined aqueous solution was reextracated 3 times with 250 ml of ethyl acetate and 3 times with 500 ml of methylene chloride. The methylene chloride solution was washed with 40 ml of water, dried over $MgSO_4$, and evaporated under reduced pressure. The residual oil was cooled at 4° C. for crystallization. The resulting solid was recrystallized from ethyl acetate/hexane to give N, N'di[2'-(2-methyl-5-nitro-1-imidazolyl)-1,4-butanediamine.

The chemical structure analysis was performed by $^1H$ NMR ($CDCl_3$, 300 MHz) δ 7.93 (s, 2H, imidazole H4); 4.38 (t, J=6.6 $H^Z$, 4H, H1'); 2.57–2.53 (m, 4H, H1, H4); 2.50 (s, 6H, imidazole Me2); 1.75 (br, s, 2H, NH, N'H); 1.40–1.39 (m, 4H, H2, H3).

EXAMPLE 3

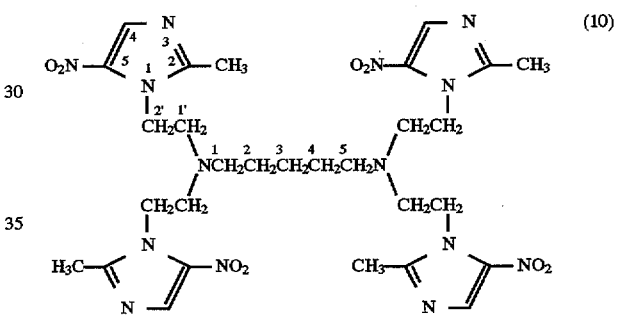

Preparation of N, N, N', N'-tetra[2'-(2-methyl-5-nitro-1-imidaolyl)ethyl]-1, 5-pentanediamine The 2-methyl-5-nitroimidazol-1-yl-acetaldehyde (3.6 g, 19.5 mmol) synthesized by the procedure described in Example 1 was dissolved in 80 ml of 1, 2-dichloroethane, 0.57 ml of pentanediamine (4.88 mmol) was added, the reaction mixture was stirred for 30 min and then acidified with 1.11 ml of acetic acid (19.5 mmol). Then 4.96 g of sodium triacetoxyborohydride (23.4 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous $NaHCO_3$ and 30 ml of water. The aqueous solution was combined for further extraction of target compound (11). The organic layer was dried over anhydrous $MgSO_4$, and the solvent was evaporated to leave residual oil which solidified at 4° C. for 2 days. The final solid was recrystallized from ethyl acetate/hexane to give N, N, N', N'-tetra[2'(2-methyl-5-nitro-1-imidazolyl) ethyl]-1, 4-pentanediamine (m.p. 150°–151° C.).

The chemical structure analysis was performed by $^1H$ NMR ($CDCl_3$, 300 $MH_Z$) δ 7.93 (s, 4H, imidazole H4); 4.24 (t, J=7.2 $H^Z$, 8H, H2'); 2.78 (t, J=7.2 $H^Z$, 8H, H1'); 2.51–2.49 (m, 4H, H1, H5); 2.49 (s, 12H, imidazole Me2); 1.26–1.20 (m, 4H, H2, H4); 1.1 (m, 2H, H3). Also the number of carbon atoms was evaluated by $^{13}C$ NMR ($CDCl_3$, 75 $MH_Z$)

δ 150.526 (imidazole C5); 138.992 (imidazole C2); 133.134 (imidazole C4); 54.599 (C2'); 54.159 (C1'); 44.964 (C1, C5); 26.964 (CH$_2$); 24.293 (CH$_2$); 14.019 (imidazole Me2).

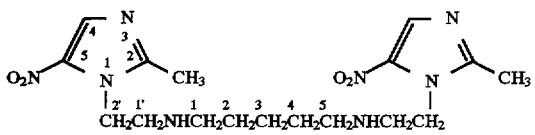
(11)

Preparation of N, N'-di[2'-(2-methyl-5-nitro-1-imidazolyl)]-1,5-pentanediamine The above combined aqueous solution was reextracted 3 times with 250 ml of ethyl acetate and 3 times with 500 ml of methylene chloride. The methylene chloride solution was washed with 40 ml of water, dried over MgSO4, and evaporated under reduced pressure. The residual oil was cooled at 4° C. to crystalize. The resulting solid was recrystallized from ethyl acetate/hexane to give N, N'-di[2'(2-methyl-5-nitro-1-imidazolyl)-1,5-pentanediamine.

The chemical structure analysis was performed by $^1$H NMR (CDCl$_3$, 300 MH$_Z$) δ 7.93 (s, 2H, imidazole H4); 4.38 (t, J=6.6 H$_Z$, 4H, H2'); 2.94 (t, J=6.6 H$_Z$, NH, N'H); 1.42–1.22 (m, 6H, H2, H3, H4).

EXAMPLE 4

Preparation of N, N, N', N'-tetra[2'(2-methyl-5-nitro-1-imidaolyl)ethyl]-1,8-octanediamine The 2-methyl-5-nitroimidazol-1-yl-acetaldehyde (3.52 g, 19 mmol) synthesized by the procedure described in Example 1 was dissolved in 80 ml of 1, 2-dichloroethane, 0.685 g of octanediamine (4.75 mmol) was added, and the reaction mixture was stirred for 30 min and then acidified with 1.08 ml of acetic acid (19 mmol). Then, 4.83 g of sodium triacetoxyborohydride (22.8 mmol) was added as a reducing agent and the solution was stirred for 48 h at room temperature. During the entire procedure the reaction vessel was gassed with nitrogen. The resulting mixture was diluted with 60 ml of ethyl acetate, and the mixture solution was washed with 85 ml of saturated aqueous NaHCO$_3$ and 30 ml of water. The aqueous solution was combined for further extraction of compound (9). The organic layer was dried over anhydrous MgSO$_4$, and the solvent was evaporated to leave residual oil which solidified at 4° C. for 2 days. The obtained solid was recrystallized from ethyl acetate/hexane to give N, N, N', N'-tetra[2'(2-methyl-5-nitro-1-imidazolyl)ethyl]-1, 8-octanediamine (m.p. 157°–158° C.).

The chemical structure analysis was performed by $^1$H NMR (CDCl$_3$, 300 MH$_Z$) δ 7.93 (s, 4H, imidazole H4); 4.26 (t, J=6.9 HZ, 8H, H2'); 2.81 (t, J=6.6Hx, 8H, H1'); 2.54–2.51 (m, 4H, H1, H8); 2.50 (s, 12H, imidazole Me2); 1.27–1.22 (m, 12H, H2, H3, H4, H5, H6, H7). Also, the number of carbon atoms present was evaluated by $^{13}$C NMR (CDCl$_3$, 75 MH$_Z$) δ 150.548 (imidazole C5); 138.908 (imidazole C2); 133.142 (imidazole C4); 54.759 (C2'); 54.045 (C1"); 44.257 (C1, C8); 29.051 (C2, C7); 26.744 (C3, C4, C5, C6); 13.951 (imidazole Me2).

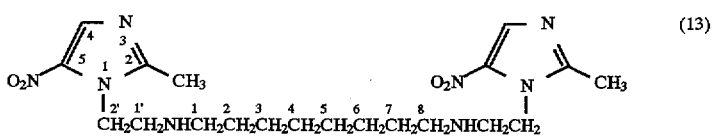
(13)

Preparation of N, N'-di[2'-(2-methyl-5-nitro-1-imidazolyl)]-1,8-octanediamine The above combined aqueous solution was reextracted 3 times with 250 ml of ethyl acetate and 3 times with 500 ml of methylene chloride. The methylene chloride solution was washed with 40 ml of water, dried over MgSO4, and evaporated under reduced pressure. The residual oil was cooled at 4° C. to crystallize. The resulting solid was recrystallized from ethyl acetate/hexane to give N, N'-d[2'-(2-methyl-5-nitro-1-imidazolyl)-1,8-octanediamine.

The chemical structure analysis was performed by $^1$H NMR (CDCl$_3$, 300 MH$_Z$) δ 7.93 (s, 2H, imidazole H4); 4.38 (t, J=6.6 H$_Z$, 4H, H2'); 2.94 (t, J=6.6 H$_Z$, 4H, H1'); 2.57–2.53 (m, 4H, H1, H8); 2.50 (s, 6H, imidazole Me2); 1.89 (br, s, 2H, NH, N'H); 1.45–1.20 (m, 12H, H2, H3, H4, H5, H6, H7).

EXAMPLE 5

Preparation of N, N, N', N'-tetra[2'-(2-methyl-5-nitro-1-imidazolyl)ethyl]-1,8-octanediamine gluconic acid salt A solution of N, N, N', N'-tetra[2'-(2-methyl-5-nitro-1-imidazolyl)ethyl]-1,8-octanediamine free base was prepared by dissolving 0.5 g of N, N, N', N'-tetra[2'-(2-methyl-5-nitro-1-imidazolyl)ethyl]-1,8-octanediamine in 20 ml of CH$_2$Cl$_2$. To this solution, 2 g of gluconic acid in 5 ml of water was added. To the resultant mixture, pure MeOH was added dropwise until the mixture became a homogeneous solution. To this, 50 ml of ether, followed by 200 ml of

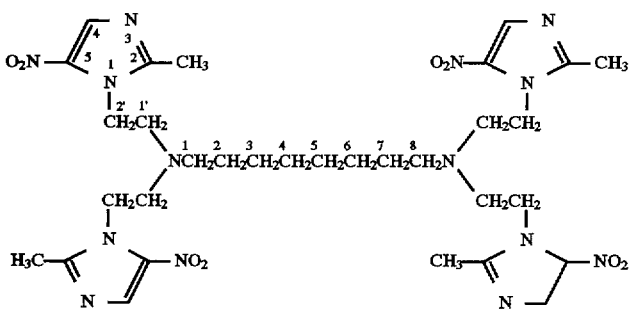
(12)

hexane were added to precipitate the solid. The reaction mixture was cooled to 4° C., the precipitated salt was removed by filtration through a sintered glass funnel, washed with anhydrous ether and dried under vacuum. This d-gluconic acid salt is highly soluble in water.

EXAMPLE 6

Radiosensitization Effects on Hypoxic Tumor Cells

The in vitro radiosensitization effects of compounds (8) and (10) were evaluated on Chinese hamster ovary (CHO) cells, and the results were compared to the effects with metronidazole. Cells were plated and allowed to attach on glass petri dishes for 3 h, then the media were replaced with 5 ml of Hank's balanced salt solution (HBSS) with or without drugs. To induce cell hypoxia, the dishes were placed at room temperature into sealed aluminum chambers (8 dishes/chamber). The chambers were degassed by pumping, and then back-filled with 95% $N_2$ and 5% $CO_2$. This procedure was repeated 4 times with 5 min holding periods under positive gas pressure between evacuations. After 1 h, when the cells were severely hypoxic, the chambers were placed in 37° C. water bath for 1 hr. For oxic treatment groups, cells were placed in 37° C. incubators for 2 h with 5 ml of HBSS (±drugs). The chambers were placed on a rotating table and exposed to an X-ray beam generated by a General Electric Maxitron 300 therapy machine operated at 250 kVp and 20 mA (HVL 20 mm Al filter; dose rate at 2 Gy/min). After irridation, cells were rinsed with HBSS, and covered with fresh media. Cells were cultured for 7 days in a 37° C. incubator. The resulting cell colonies were stained and counted. The results are shown in Tables 1 and 2.

TABLE 1

Radiosensitization Efficacy of Compounds (8) and (10) on CHO Cells. For Comparison, Values Obtained with Metronidazole are also Shown.

| Compounds | Drug Dose (mM) | SER[a] (N2) | SFR[b] (N2) (18 Gy) | Ratio of RT[c] Dose For 0.04 SF[d] | Do (Gy) |
|---|---|---|---|---|---|
| 8 | 0.1 | 1.3 | 9.0 | 1.5 | 2.5 |
| 10 | 0.1 | 1.6 | 21.4 | 1.5 | 1.9 |
| Metronidazole | 0.5 | 1.0 | 1.9 | 1.1 | 3.3 |
| $N_2$ | - | - | - | - | 3.3 |
| $O_2$ | - | - | - | - | 1.4 |

[a] = Sensitizer enhancement ratio is the ratio of the Do for irradiation under hypoxic conditions without the drug divided by the Do with the drug
[b] = Surviving fraction ratio is the ratio of surviving fractions produced by a given radiation dose with and without the drug.
[c] = Radiation therapy
[d] = Surviving fraction

TABLE 2

Radiosensitization Potency of Compounds (8) and (10) on CHO Cells as Compared to Metronidazole

| Compound | Sensitization Ratio at 20% Survival Level |
|---|---|
| 8 | 50 |
| 10 | 400 |

In the experiment shown in Table 2 hypoxic CHO cells were irradiated with a single X ray dose of 8 Gy, with or without drugs. The drug molarity required to reduce cell survival to 20% of the untreated control value was 10 mM for metronidazole, 0.2 mM for compound (8), and 0.025 mM for compound (10). In other words, compound (8) was 50 times and compound (10) was 400 times more potent than metronidazole.

Combined Drug/Heat Effects

To examine the thermo-radiosensitizing effects of compounds (8) and (10), hypoxic CHO cells were irradiated (with or without drugs) with radiation doses ranging from 0–30 Gy. After irradiation, the chambers were placed either in a 37° C. or in a 41° C. water bath for 30 min. Then cell survival was evaluated by the colony forming assay. The results are presented in Table 3.

TABLE 3

Thermo-radiosensitization Effects of Compounds (8) and (10) on CHO Cells in Presence of Heat (41° C., 30 min)

| Compounds | Drug Dose (µM) | Do (Gy) |
|---|---|---|
| 8 | 50 | 0.8 |
| 10 | 10 | 0.6 |
| $O_2$ | — | 1.6 |
| $N_2$ | — | 4.0 |

From the results shown in Table 3 it is clear that combining administration of compounds (8) or (10) with mild hyperthermia is even more effective in radiosensitizing CHO cells than treatment with drugs alone. In fact, the magnitude of the combined sensitization effect is such that hypoxic cells become even more radiosensitive (smaller $D_O$) than fully oxic cells.

EXAMPLE 7

Toxicity Data (1) In Vitro 0.2 mM diaminetetrametronidazole (DATM) (formula 8) and 10 mM metro were administered for 2 hours at 4° C. and found to be equally effective at these dosages in radiosensitizing hypoxic CHO cells. Subsequently, hypoxic CHO cells were incubated with 0.2 mM DATM or 10 mM metro for 12 hours at 37° C. No toxic effects were noted for the CHO cells incubated with the DATM, while the CHO cells incubated with the metro exhibited a 95% reduction in colony formation.

(2) In Vivo

In a preliminary in vivo study, two groups of mice were injected intraperitoneally with either 1 g/kg or 4 g/kg of DATM (formula 8). No toxicity was observed in the 1 g/kg group, but all mice of the 4 g/kg group died. By comparison, the $LD_{50}$ (lethal dose of 50% of animals) for metro is reported to be about 3.3 g/kg. Hence, the toxicity of DATM appears to be roughly comparable to that of metro for the same dosage, yet its radiosensitizing potency is substantially higher.

In view of the above, it will be seen that the several objects of the invention are achieved and other advantageous results attained.

As various changes could be made in the above compounds and methods without departing from the scope of the invention it is intended that all matter contained in the above description shall be interpreted as illustrative and not in a limiting sense.

What is claimed is:

1. A compound having the formula

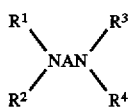

wherein A comprises a carbon chain having from about 4–10 carbons in the chain, $R^1$, $R^2$, $R^3$, and $R^4$ are

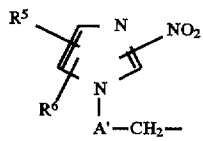

wherein A' comprises a carbon chain having from about 1–8 carbons in the chain, $R^5$ is H, lower alkyl, or halo, and $R^6$ is H, lower alkyl, halo or nitro, or a salt of said compound.

2. A compound having the formula

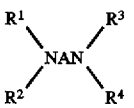

wherein A comprises a carbon chain having from about 2–10 carbons in the chain, $R^1$, $R^2$, $R^3$, and $R^4$ are

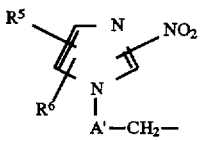

wherein A' comprises a carbon chain having from about 1–8 carbons in the chain, $R^5$ is H, lower alkyl, or halo, and $R^6$ is H, lower alkyl, halo or nitro, or a salt of said compound.

3. A compound or a salt thereof as set forth in claim 2 wherein $R^1$, $R^2$, $R^3$, and $R^4$ are each a 2-nitroimidazolyl alkyl group.

4. A compound or a salt thereof as set forth in claim 2 wherein $R^1$, $R^2$, $R^3$, and $R^4$ are each a 4-nitroimidazolyl alkyl group.

5. A compound or a salt thereof as set forth in claim 2 wherein $R^1$, $R^2$, $R^3$, and $R^4$ are each a 5-nitroimidazolyl alkyl group.

6. A compound or a salt thereof as set forth in claim 5 wherein $R^5$ is 2-methyl and $R^6$ is H.

7. A compound or a salt thereof as set forth in claim 6 wherein A' is methylene.

8. A compound as set forth in claim 7 which is N, N, N', N'-tetra[2'-(2-methyl-5-nitro-1-imidazolyl)ethyl]-1,4-butanediamine, or a salt thereof.

9. A compound as set forth in claim 7 which is N, N, N', N'-tetra[2'-(2-methyl-5-nitro-1-imidazolyl)ethyl]-1,5-pentanediamine, or a salt thereof.

10. A compound as set forth in claim 7 which is N, N, N', N'-tetra[2'-(2-methyl-5-nitro-1-imidazolyl)ethyl]-1,8-octanediamine, or a salt thereof.

11. A compound or a salt thereof, the compound having the formula:

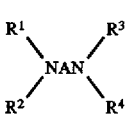

wherein A is a hydrocarbon chain having from 2 to about 10 carbons in the chain, $R^1$ and $R^4$ are H, and $R^2$ and $R^3$ have the formula:

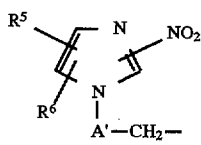

wherein A' is a hydrocarbon chain having from about 1 to 8 carbons in the chain, $R^5$ is H, lower alkyl, or halo, and $R^6$ is H, lower alkyl, halo or nitro.

12. A compound or a salt thereof as set forth in claim 11 wherein $R^2$ and $R^3$ are each a 2-nitroimidazolyl alkyl group.

13. A compound or a salt thereof as set forth in claim 11 wherein $R^2$ and $R^3$ are each a 4-nitroimidazolyl alkyl group.

14. A compound or a salt thereof as set forth in claim 11 wherein $R^2$ and $R^3$ are each a 5-nitroimidazolyl alkyl group.

15. A compound or a salt thereof as set forth in claim 14 wherein $R^5$ is 2-methyl.

16. A compound or a salt thereof as set forth in claim 15 wherein A' is methylene.

17. A compound or a salt thereof, the compound being N, N'-di[2'-(2-methyl-5-nitro-1-imidazolyl)ethyl]-1,4-butanediamine.

18. A compound or a salt thereof, the compound being N, N'-di[2'-(2-methyl-5-nitro-1-imidazolyl)ethyl]-1,5-pentanediamine.

19. A compound or a salt thereof, the compound being N, N'-di[2'-(2-methyl-5-nitro-1-imidazolyl)ethyl]-1,8-octanediamine.

20. A pharmaceutical composition for radiosensitizing hypoxic cells comprising a radiosensitizing amount of a compound comprising the compound of claim 1 or a pharmaceutically acceptable salt thereof in admixture with a pharmaceutically acceptable carrier.

21. A pharmaceutical composition for radiosensitizing hypoxic cells comprising a radiosensitizing amount of a compound or a pharmaceutically acceptable salt thereof in admixture with a pharmaceutically acceptable carrier, the compound having the formula

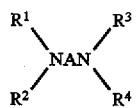

wherein A comprises a carbon chain having from about 2–10 carbons in the chain, $R^1$, $R^2$, $R^3$, and $R^4$ are

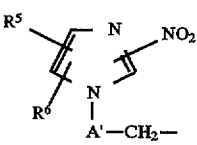

wherein A' comprises a carbon chain having from about 1–8 carbons in the chain, $R^5$ is H, lower alkyl, or halo, and $R^6$ is hydrogen, lower alkyl, halo or nitro.

22. A pharmaceutical composition as set forth in claim 21 wherein the compound is N, N, N', N'-tetra[2'-(2-methyl-5-nitro-1-imidazolyl)ethyl]-1,4-butanediamine.

23. A pharmaceutical composition as set forth in claim 21 wherein the compound is N, N, N', N'-tetra[2'-(2-methyl-5-nitro-1-imidazolyl)ethyl]-1,5-pentanediamine.

24. A method of radiosensitizing hypoxic tumor cells which comprises administering a radiosensitizing amount of a pharmaceutical composition as set forth in claim 21.

25. A method as set forth in claim 24 which further comprises heat treating the hypoxic tumor cells.

26. A method of killing hypoxic tumor cells in a warm-blooded animal, the method comprising:
   (a) administering to the warm-blooded animal a pharmaceutical composition as set forth in claim 21 in an amount effective to radiosensitize the hypoxic tumor cells,
   (b) followed by, after a time interval sufficient to enhance radiosensitization of the hypoxic tumor cells, irradiating the hypoxic tumor cells with a dose of radiation effective to kill the hypoxic tumor cells.

27. A method as set forth in claim 26 further comprising heat treating the hypoxic tumor cells.

28. A pharmaceutical composition for radiosensitizing hypoxic cells comprising a radiosensitizing amount of a compound or a pharmaceutically acceptable salt thereof in admixture with a pharmaceutically acceptable carrier, the compound having the formula:

 (1)

wherein A is a hydrocarbon chain having from 2 to about 10 carbons in the chain, $R^1$ and $R^4$ are H, and $R^2$ and $R^3$ have the formula:

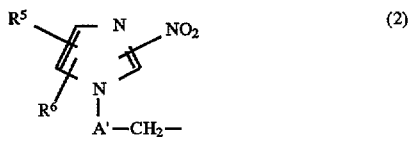 (2)

wherein A' is a hydrocarbon chain having from about 1 to 8 carbons in the chain, $R^5$ is H, lower alkyl, or halo, and $R^6$ is H, lower alkyl, halo or nitro.

29. A method of radiosensitizing hypoxic tumor cells which comprises administering a radiosensitizing amount of a pharmaceutical composition as set forth in claim 28.

30. A method of killing hypoxic tumor cells in a warm-blooded animal, the method comprising:

(a) administering to the warm-blooded animal a pharmaceutical composition as set forth in claim 28 in an amount effective to radiosensitize the hypoxic tumor cells,
   (b) followed by, after a time interval sufficient to enhance radiosensitization of the hypoxic tumor cells, irradiating the hypoxic tumor cells with a dose of radiation effective to kill the hypoxic tumor cells.

31. The compound or a salt of claim 1 wherein $R^5$ is methyl and $R^6$ is H.

32. The compound or a salt of claim 31 wherein A' is methylene.

33. The compound or a salt of claim 1 wherein A' is methylene.

* * * * *